United States Patent [19]

Hetzel et al.

[11] B 4,001,273

[45] Jan. 4, 1977

[54] CONTINUOUS MANUFACTURE OF PHTHALIMIDE

[75] Inventors: Eckhard Hetzel; Ludwig Vogel, both of Frankenthal; Gerhard Rotermund, Heidelberg; Hans Christoph Horn, Lambsheim, all of Germany

[73] Assignee: BASF Aktiengesellschaft, Ludwigshafen (Rhine), Germany

[22] Filed: July 8, 1974

[21] Appl. No.: 486,678

[44] Published under the second Trial Voluntary Protest Program on March 2, 1976 as document No. B 486,678.

[30] Foreign Application Priority Data

July 10, 1973 Germany ............................ 2334916

[52] U.S. Cl. .......................................... 260/326 R
[51] Int. Cl.$^2$ ...................................... C07D 209/48
[58] Field of Search .............................. 260/326 R

[56] References Cited

UNITED STATES PATENTS 2,566,992  9/1951  Morgan et al. ................ 260/326 R

FOREIGN PATENTS OR APPLICATIONS 300,770  8/1972  Austria .......................... 260/326 R

OTHER PUBLICATIONS

Pfeifer et al., "Chem. Abstracts," vol. 77, p. 353, No. 126,087s (1972).

*Primary Examiner*—Elbert L. Roberts
*Assistant Examiner*—S. P. Williams
*Attorney, Agent, or Firm*—Johnston, Keil, Thompson & Shurtleff

[57] ABSTRACT

Continuous manufacture of phthalimide by reaction of phthalic anhydride with ammonia and washing the offgas with a melt containing phthalimide. The product is a starting material for the manufacture of dyes, pesticides and pigments, especially copper phthalocyanines.

7 Claims, No Drawings

CONTINUOUS MANUFACTURE OF PHTHALIMIDE

This application discloses and claims subject matter described in German Patent Application No. 2334916, filed July 10, 1973, which is incorporated herein by reference.

The invention is concerned with a process for the continuous manufacture of phthalimide by reaction of phthalic anhydride with ammonia and washing the off-gas with a melt containing phthalimide.

U.S. Pat. No. 2,668,326 describes a method of reacting phthalic anhydride and ammonia batchwise and washing the off-gases from the reaction with water or a high-boiling hydrocarbon as the solvent. It is advantageous to recycle the wash fluid, resulting in accumulation of suspended phthalimide. This suspension is also used for cooling and quenching the hot reaction mixture.

German Published Specification DOS No. 2,056,891 describes a process in which phthalic anhydride and excess ammonia are reacted continuously in cocurrent. The reaction mixture enters a sublimation chamber where phthalimide is precipitated by cooling and the uncondensed portions of phthalimide, phthalic anhydride and by-products, and ammonia and water vapor, are lead off through a gas baffle.

In all these cases, the off-gas still retains some phthalic anhydride, which at the least accounts for more than 5% by weight, but frequently more than 20% by weight, of the off-gas, and this is unsatisfactory, particularly in industrial operation. In the continuous process, the off-gas in general contains water vapor, 5 to 35% by weight of phthalic anhydride, 20 to 40% by weight of phthalimide and 3 to 10% by weight of ammonia, based on the total amount of off-gas.

It is an object of the present invention to provide a simpler and more economical process for the manufacture of phthalimide which gives better yields of higher purity product.

We have found that phthalimide is obtained under advantageous conditions by continuous reaction of phthalic anhydride with ammonia at elevated temperature and washing of the off-gas, when the off-gas from the reaction is washed with a melt containing at least 70% by weight of phthalimide, at a temperature of not less than 210°C, and the melt is then recycled to the reaction.

The reaction can be represented by the following equation:

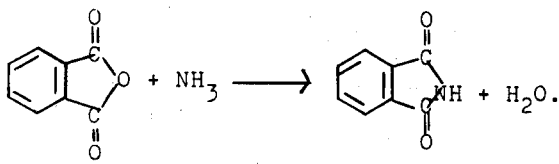

Surprisingly, the process according to the invention gives phthalimide more simply and economically, and in better yield and purity, than do the conventional processes. After washing, the off-gas retains at most 1.5% by weight, and in most cases less than 0.3% by weight, of phthalic anhydride, and at most 70% by weight, and in most cases less than 65% by weight, of phthalimide. Essentially, the off-gas has thus been freed from by-products and the proportion of phthalimide has been increased. Such an off-gas can be used with advantage for numerous syntheses; since the off-gas is conveniently trapped in aqueous alkali, for example in sodium hydroxide solution, or potassium hydroxide solution, of from 5 to 20 per cent strength by weight, in which phthalimide dissolves, such solutions can be used direct, for example, as feedstock for the synthesis of anthranilic acid and isatoic anhydride by reaction of alkali metal phthalimides with alkali metal hypochlorite. On the other hand, even a small proportion of phthalic anhydride would also dissolve in alkali and would result in impure end products being obtained from the subsequent synthesis, necessitating costly and involved purification operations causing substantial losses of end product. Since the melt according to the invention, used for washing, essentially dissolves the abovementioned by-products and thus causes them to be recycled to the manufacture of phthalimide, a better yield of end product is achieved.

The reaction of phthalic anhydride with ammonia can be carried out in the reaction chamber in cocurrent, for example in accordance with the process described in German Published Specification No. 2,056,689; and off-gas of the above composition results. However, it is more advantageous to react the starting materials in countercurrent in accordance with the process described in German Patent Application No. 2334379.

The reaction in countercurrent is generally carried out using a molar ratio from 0.9 to 1.1, preferably from 1 to 1.04, and in particular 1 mole of ammonia per 1 mole of phthalic anhdride, at atmospheric or superatmospheric pressure, suitably at temperatures from 135°C to 300°C and preferably at temperatures from 150° to 250°C. It is possible to use pure phthalic anhydride or technical phthalic anhydride, for example containing 90 to 95% by weight of phthalic anhydride, as obtained from the manufacturing process, for example by catalytic oxidation of naphthalene with air. Equally, the ammonia can be employed as a mixture with inert gases, for example with nitrogen or carbon dioxide. In general, phthalic anhydride melt is charged into the reactor at a throughput of 800 to 3,000, preferably 1,700 to 2,200, kg per hour per square meter of reactor cross-section. The reactors used can be stirred kettle cascades, advantageously comprising from 3 to 6 stirred kettles connected in series, or columns of which a part acts as a stirred kettle, whilst the lower part is so designed that the reactants react with one another without appreciable backmixing. For example, tray columns or bubble columns are used, in which the lower part of the column is filled with packing. It is also possible to use a stirred vessel followed by a countercurrent column. The columns used can be sieve tray columns, Oldershaw columns, glass tray columns, bubble cap tray columns, valve tray columns, packed columns or columns with rotating inserts. It is advantageous to use tray columns which permit the abovementioned rate of input of the anhydride melt. In bubble cap tray columns the preferred ratio of weir height to diameter is from 0.2 to 0.4, whilst in ball valve tray columns and sieve tray columns, hole diameters from 5 to 15 mm, ball diameters from 8 to 30 mm and tray spacings of 300 to 800 mm are preferred. The tray columns preferably comprise from 8 to 14 trays. The melt is conveniently allowed to enter the column head through an atomizer or through jets. It is advantageous to allow the reaction temperature to rise from the melt inlet, for example the column top, to the inlet of the stream of ammonia gas, for example through a jet at the bottom of the column; a temperature of at least 150°C, and in particular from 150° to 210°C, at the top, and of at most 270°C, and in particular from 240° to 265°C, at the bottom of the column, with a continuous rise in temperature down the column, is suitable. The throughput of ammonia is suitably from 90 to 280 kg, and preferably from 160 to 220 kg, per hour per square meter of column cross-section. The charge of packing, for example rings, cylinders, saddles, wire mesh rings, helices, coils, spheres or, preferably, rings of 30 to 80 mm diameter, advantageously occupies the bottom quarter to bottom third of the total space in the reactor.

The reaction can be carried out as follows: the two starting materials are reacted with one another in the above manner in countercurrent in a column, at the reaction temperature. At the bottom of the column, the reaction mixture essentially crude phthalimide, is withdrawn as a melt, cooled, for example on a cooling drum or cooled belt, and conveniently isolated in flake form. The off-gas issues at the top of the column.

In general, the off-gas from the cocurrent process contains 15 to 35% by weight of water vapor and the abovementioned proportions of ammonia and phthalic acid or its derivatives, whilst the above countercurrent process the off-gas contains 40 to 60% by weight of water vapor, 0.3 to 1% by weight of ammonia, 35 to 50% by weight of phthalic anhydride and, depending on the reaction temperature, 0 to 6% by weight of phthalic acid, 0.3 to 1% by weight of phthalimide, 0 to 8% by weight of monoammonium phthalate and 0 to 10% by weight of diammonium phthalate. The off-gas can be washed with a melt of pure phthalimide or technical phthalimide. For example, the crude phthalimide obtained as the end product from the batchwise reaction of phthalic anhydride with ammonia can also be used in the form of its melt; such a phthalimide in general contains 0.1 to 0.3% by weight of water vapor, 0.1 to 0.3% by weight of ammonia, 1 to 20% by weight of phthalic anhydride, 0 to 20% by weight of phthalic acid, 80 to 90% by weight of phthalimide, 0 to 20% by weight of monoammonium phthalate and 0 to 20% by weight of diammonium phthalate. However, melts of continuously manufactured phthalimide are preferred as the wash liquid. The above phthalimide, manufactured continuously in cocurrent, in general contains, in the melt, 0.1 to 0.3% by weight of water vapor, 0.1 to 0.3% by weight of ammonia and 10 to 20% by weight of phthalic anhydride. However, in the preferred embodiment of the process, melts of the above phthalimide manufactured continuously in countercurrent are used; these in general contain 0 to 0.001% by weight of water vapor, 0.1 to 0.3% by weight of ammonia, 0.1 to 0.5% by weight of phthalic anhydride and 98 to 99.8% by weight of phthalimide.

As a rule, the washing process is carried out batchwise or, preferably, continuously, at temperatures not below 210°C, advantageously from 240° to 260°C, and preferably from 245° to 255°C, at atmospheric or superatmospheric pressure. The melt is preferably at a temperature from 210° to 270°C, preferably from 245° to 260°C, and preferably contains from 95 to 100, and in particular from 99.1 to 99.7% by weight of phthalimide. Suitable washing rates are from 0.2 to 0.06, preferably from 0.12 to 0.08, part of off-gas per part of melt, and a throughput of 5,000 to 1,500 kg of melt per hour per square meter of the washing unit. In general, the above columns, especially packed columns with from 2 to 4 theoretical plates, are used as the wash unit.

The wash can be effected as follows: phthalic anhydride and ammonia are reacted continuously in countercurrent in the above manner, and the gases formed pass, as off-gas, from the top of the reactor to the bottom of the wash column. The off-gas passing upward in the wash column now encounters, in countercurrent, the melt which is preferably fed to the top of the wash column by means of an atomizer, for example spray jets. At the bottom of the wash column, the melt which accumulates is then withdrawn and fed to the top, or one of the trays, of the reactor, preferably the tray which contains a reaction mixture of similar composition. For example, the melt recycled to the reaction can contain from 5 to 20% by weight of phthalic anhydride, and in the case of a column with 8 to 14 trays, trays 2 to 4 (counted from the top of the column) in general have a similar content of phthalic anhydride in the crude phthalimide and can therefore be considered as suitable points of entry of the melt. Preferably, 50 to 80% by weight of the reaction mixture issuing at the bottom of the reactor are withdrawn continuously and fed, as a melt at the above temperature, to the top of the wash column. The end product is isolated from the residual reaction mixture by conventional methods, for example by crystallization, or the reaction mixture is fed direct to further syntheses; for example, it can be dissolved in aqueous alkali and used as a starting material for the manufacture of anthranilic acid.

In the countercurrent process, the wash column can also be combined with the reaction column, for example by using a column with from 14 to 20 trays, feeding phthalic anhydride melt continuously to tray 6 and introducing ammonia at the bottom of the column and melt, as wash fluid, at the top of the column. In this embodiment, the melt, after washing the off-gas on trays 1 to 6, can be fed to tray 6 (phthalic anhydride melt) or to a tray containing a reaction mixture of similar composition. In other respects, the wash and reaction are carried out in the above manner.

Preferably, the washed off-gas, which in general contains 35 to 40% by weight of water vapor, 0.1 to 0.3% by weight of ammonia and 0.1 to 0.3% by weight of phthalic anhydride is withdrawn from the top of the wash column. Since significant amounts of phthalic anhydride and other byproducts are no longer present, the off-gas can be processed further directly; for example, it is dissolved in aqueous alkali and the solution is used to manufacture anthranilic acid. It is also possible to quench the off-gas with water and to filter the suspension formed to obtain the phthalimide which has separated out. The off-gas can also be used for the manufacture of a phthalocyanine, for example by passing it into the melt or into a solution, such as a solution in nitrobenzene or trichlorobenzene, of urea, phthalic anhydride or phthalimide, ammonium molybdate and metal salt.

The phthalimide which can be manufactured by the process of the invention is a valuable starting material for the manufacture of dyes, pesticides and pigments, especially copper phthalocyanines. It is also used as a stabilizer additive in aviation fuels. Details of its use may be found in Ullmanns Encyklopadie der technischen Chemie, volume 13, page 735.

The parts in the Examples which follow are parts by weight. They bear the same relation to parts by volume as the kilogram to the liter.

EXAMPLE 1

A bubble-cap tray column with 10 trays is used as the reactor. 148 parts of phthalic anhydride are fed in hourly at the top of the column and 17 parts of ammonia at the bottom, and the temperature at the uppermost tray is maintained at 190°C and that at the lowest tray at 249°C. During the reaction, in which the starting materials flow in countercurrent, 318 parts of the reaction mixture are withdrawn hourly from the bottoms. The off-gas (30 parts per hour) contains 60% by weight of water vapor, 0.5% by weight of ammonia, 39% by weight of phthalic anhydride and 0.5% by weight of phthalimide. It is washed continuously, with 200 parts of melt (99% by weight of phthalimide) per hour at 250°C, in a further 4-tray wash column. 182 parts of bottoms liquid are withdrawn hourly from the wash column and fed to the seventh tray (counted from the top) of the reactor. 200 parts of the reaction mixture withdrawn from the bottoms of the reactor are fed hourly, as a melt at 249°C, to the top of the wash column. The remainder of the reaction mixture (118 parts per hour) is cooled. 110 parts of phthalimide, of melting point from 234° to 238°C, are obtained hourly.

The washed off-gas (48 parts per hour) now contains 37.5% by weight of water vapor, 0.3% by weight of ammonia, 0.2% of phthalic anhydride and 62% by weight of phthalimide and is dissolved direct in aqueous alkali and used for the synthesis of anthranilic acid.

EXAMPLE 2 (COMPARISON)

If the reaction is carried out without washing and recycling of the wash fluid to the reactor analogously to Example 1, the off-gas (30 parts per hour) contains 60% by weight of water vapor, 0.5% by weight of ammonia, 39% by weight of phthalic anhydride and 0.5% by weight of phthalimide.

We claim:

1. A process for the continuous manufacture of phthalimide which comprises reacting phthalic anhydride with ammonia at a temperature of from about 135°C. to 300°C., washing the off-gas with a melt of substantially pure phthalimide or a melt of crude phthalimide obtained as the end product from the reaction of phthalic anhydride with ammonia and containing at least 70% by weight of phthalimide, at a temperature of not less than 210°C, and then recycling the melt to the reaction.

2. A process as claimed in claim 1, wherein the reaction is carried out in countercurrent with a molar ratio of 0.9 to 1.1 moles of ammonia per 1 mole of phthalic anhydride, at a temperature from 150°C to 250°C.

3. A process as claimed in claim 1, wherein the wash is carried out with melts of phthalimide which have been produced continuously in countercurrent.

4. A process as claimed in claim 1, wherein the wash is carried out at a temperature from 240° to 260°C.

5. A process as claimed in claim 1, wherein the wash is carried out at a temperature from 245° to 255°C.

6. A process as claimed in claim 1, wherein the wash is carried out at a throughput of from 5,000 to 1,500 kg of melt per hour per square meter of cross-section of the wash unit.

7. A process as claimed in claim 1, wherein the reaction is carried out in countercurrent and the wash column is combined with the reactor by using a tray column, feeding phthalic anhydride melt continuously to one of the middle trays and introducing ammonia at the bottom of the column and melt, as the wash fluid, at the top of the column.

* * * * *